United States Patent

Bannister et al.

[11] Patent Number: 5,892,093
[45] Date of Patent: Apr. 6, 1999

[54] RESOLUTION

[75] Inventors: Robin Mark Bannister; Graham Robert Evans; Benjamin Mark Skead, all of Cambridge, United Kingdom

[73] Assignee: Darwin Discovery Limited, United Kingdom

[21] Appl. No.: 796,358

[22] Filed: Feb. 7, 1997

Related U.S. Application Data

[60] Provisional application No. 60/016,536, May 7, 1996 and provisional application No. 60/016,987, May 7, 1996.

[30] Foreign Application Priority Data

Feb. 8, 1996 [GB] United Kingdom .................... 9602514
Feb. 8, 1996 [GB] United Kingdom .................... 9602515

[51] Int. Cl.[6] ................................................. C07C 255/03
[52] U.S. Cl. ........................................... 558/354; 558/406
[58] Field of Search ..................................... 558/406, 354

[56] References Cited

FOREIGN PATENT DOCUMENTS 2059923 12/1972 Germany .
1367677 9/1974 United Kingdom .
9509150 4/1995 WIPO .

*Primary Examiner*—Johann Richter
*Assistant Examiner*—Ebenezer Sackey
*Attorney, Agent, or Firm*—Saliwanchik, Lloyd & Saliwanchik

[57] ABSTRACT

A reproducible process for preparing a substantially single enantiomer (R or S) of 4-cyano-4-(3,4-dimethoxyphenyl)-5-methylhexanoic acid, or an analogue thereof, thereby providing single enantiomer acid for the first time, proceeds by means of a classical salt resolution employing a resolving agent selected from an enantiomer (R or S) of a 1-arylalkylamine and (−)-quinine, and provides novel salts that are readily convertible to verapamil.

3 Claims, No Drawings

RESOLUTION

CROSS-REFERENCE TO RELATED APPLICATION

This application claims the benefit of U.S. Provisional Application No. 60/016,536, filed May 7, 1996, and U.S. Provisional Application No. 60/016,987, filed May 7, 1996.

FIELD OF THE INVENTION

The present invention relates to processes for the manufacture of single enantiomer and enantiomerically-enriched forms of verapamil precursors, and their use in the manufacture of verapamil.

BACKGROUND OF THE INVENTION

Verapamil (1, below) is presently in clinical use as the racemate and is used extensively for the treatment of hypertension. The (S)-enantiomer (levoverapamil) has the majority of the calcium channel antagonist activity (see DE-A-2059923), whilst the (R)-enantiomer (dextroverapamil) differs in having sodium channel and other cell-pump actions in addition to higher bioavailability, with slower clearance rate. Therefore, single isomer products may have clinical utility. For example, the (R)-enantiomer may be of benefit for the treatment of multidrug resistance in cancer chemotherapy (see Eliason, Int. J. Cancer (1990) 46: 113).

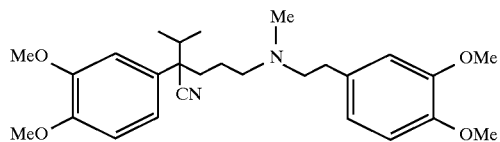

(1)

There is, therefore, a requirement for efficient processes to manufacture enantiomerically-enriched forms of verapamil and its analogues. This is a challenging endeavour since construction of the quaternary chiral centre with high asymmetric induction is difficult. Several synthetic routes have been published, but for a variety of reasons these are not suitable for operation on a large scale.

For example, Theodore and Nelson, J. Org. Chem. (1987) 52:1309, describe a synthesis of (S)-verapamil commencing from (S)-1,2-propanediol which entails eleven steps, only three of which are used to create permanent skeletal bonds. Of the shorter routes proceeding via classical resolution, a process reported in WO-A-9509150, involving resolution of the secondary amine intermediate and subsequent conversion to single enantiomer verapamil, is advantageous over resolution or verapamil itself, which is described in DE-A-3723684 and WO-A-9316035, due to better atom utilisation and lower waste levels.

Alternatively, resolution of a racemic acid precursor would appear to provide an attractive route. Indeed, resolution of 4-cyano-4-(3,4-dimethoxyphenyl)-5-methylhexanoic acid (verapamilic acid 2, below) has already been reported in DE-A-2059923 using brucine, together with elaboration to enantiomerically-enriched verapamil. However, there is doubt as to whether this resolution process is reproducible. In addition, brucine is highly toxic, and thus unsuitable for a large-scale manufacturing process.

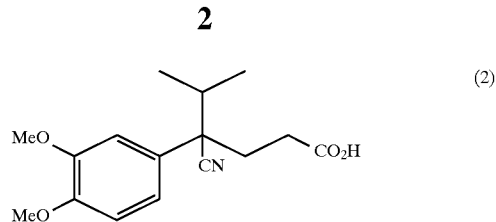

(2)

SUMMARY OF THE INVENTION

According to a first aspect of the present invention, a process for preparing a substantially single enantiomer (R or S) of 4-cyano-4-(3,4-dimethoxyphenyl)-5-methyl-hexanoic acid, or an analogue thereof, proceeds by means of a classical salt resolution employing an enantiomer (R or S) of an industrially-acceptable resolving agent that is a 1-arylalkylamine or (−)-quinine. The product obtained from the resolution can then, if desired, be converted to single enantiomer verapamil by standard chemical techniques.

The resolving agents for use in the present invention are more industrially-acceptable than the formerly used brucine. In particular, they are relatively non-toxic as compared to brucine, and tend not to require special handling techniques. They are, therefore, suitable for large-scale, i.e. multi-tonne, manufacture. Further, such resolving agents are available in large quantities at reasonable cost, which is again advantageous for large-scale manufacture, and are robust enough to withstand recycling and several passes through the resolution process.

In addition, the doubtful reproducibility of the brucine resolution means that access to a substantially single enantiomer (R or S) of 4-cyano-4-(3,4-dimethoxyphenyl)-5-methylhexanoic acid is reliant on the process of the present invention. The substantially single enantiomer form of the acid is thus enabled for the first time.

According to a second aspect of the present invention, novel salts of 4-cyano-4-(3,4-dimethoxyphenyl)-5-methylhexanoic acid, or an analogue thereof, are provided.

DESCRIPTION OF THE INVENTION

Preferred 1-arylalkylamines include those in which the aryl group has 6 to 20 carbon atoms, e.g. naphthyl or phenyl. More preferred are the 1-arylethylamines, with 1-(1-naphthyl)ethylamine and 1-phenylethylamine (otherwise known as α-methylbenzylamine) being particularly preferred.

The resolution procedure is extremely simple. For example, a quantity of racemic 4-cyano-4-(3,4-dimethoxyphenyl)-5-methylhexanoic acid and a quantity of resolving agent are suspended in a suitable solvent, warmed, e.g. to about 40° C., and then cooled, e.g. to about 15° C., whereupon a crystalline solid, i.e. a salt, forms. This crystalline material will be enriched in either (R) or (S)-4-cyano-4-(3,4-dimethoxyphenyl)-5-methylhexanoic acid, depending on which resolving agent or which enantiomer of resolving agent is used. For instance, the use of (R) or (S)-1-(1-naphthyl) ethylamine or (R) or (S)-1-phenylethylamine gives rise to crystalline material, i.e. a salt, that is similarly enriched, i.e. in the (R) or (S)-enantiomer, respectively. Whereas treatment with (−)-quinine results in a crystalline material enriched in (S)-4-cyano-4-(3,4-dimethoxyphenyl)-5-methylhexanoic acid. Liberation of the free acid from the salt and recovery of the resolving agent is facilitated through standard pH adjustment and solvent extractions.

The process of the present invention is capable of achieving substantially single enantiomer 4-cyano-4-(3,4- dimethoxyphenyl)-5-methylhexanoic acid. By substantially single enantiomer typically we mean an enantiomeric excess of at least 50%, more typically at least 70%, and preferably higher, e.g. at least 80% or 90% ee. The enantiomeric excess of the product can be increased by standard recrystallisation techniques.

The free acid obtained by the resolution can be readily converted to verapamil, or an analogue thereof, by standard chemical techniques, for instance as described in DE-A-2059923, or more advantageously as described in British Patent Application no. 9618835.4.

The present invention is further illustrated by the following Examples. "The acid" is 4-cyano-4-(3,4-dimethoxyphenyl)-5-methylhexanoic acid.

EXAMPLE 1

The acid (2.91 g, 1.0 mmol) was taken up in 12 ml of ethanol by heating to 40° C. To this stirred solution was added (R)-1-(1-naphthyl)ethylamine (1.71 g; 1.0 mmol) in one portion via syringe. Stirring at 40° C. was continued for 5 minutes, the solution was then cooled to 15° C. and maintained at this temperature for 16 hours. A seed was added after 5 minutes stirring at 15° C. The crystals that formed were collected by filtration to give 1.10 g of a white solid, which was enriched in the (R)-enantiomer of the acid (98.3% ee as determined by chiral HPLC after salt cracking). The salt was recrystallised to diastereomeric purity with ethyl acetate.

The mother liquors from the filtration were evaporated under reduced pressure to give 3.51 g of a beige coloured solid, which was enriched with the (S)-enantiomer of the acid (50% ee).

EXAMPLE 2

This resolution was carried out according to the procedure of Example 1, except that ethyl acetate was the solvent employed.

The acid (1.70 g; 5.83 mmol) and (S)-1-(1-naphthyl)-ethylamine (1.00 g; 5.83 mmol) were taken up in 12 ml of ethyl acetate. After overnight stirring at 15° C. a precipitate had formed. This was collected by filtration to give 1.29 g of a white solid, which was enriched in the (S)-enantiomer of the acid (70.3% ee) This was recrystallised to diastereomeric purity with ethyl acetate, The mother liquors after solvent removal gave 1.40 g of a beige-coloured solid, which was enriched in the (R)-enantiomer of the acid (75% ee).

EXAMPLE 3

This resolution was carried out using the procedure of Example 1, except that ethyl acetate was the solvent employed.

The acid (0.291 g; 1.00 mmol) and (5)-1-phenylethylamine (0.121 g; 1.00 mmol) were taken up in 2 ml of ethyl acetate. The mixture was seeded after stirring at room temperature for 5 minutes. After stirring overnight at ~10° C., a precipitate had formed. This was collected by filtration to give 0.119 g of a white solid, which was enriched in the (S)-enantiomer of the acid (95% ee).

The mother liquors after solvent removal gave 0.290 g of a beige-coloured foam, which was enriched in the (R)-enantiomer of the acid (42.6% ee).

EXAMPLE 4

This resolution was carried out using the procedure of Example 1, except that isopropanol was the solvent employed.

The acid (0.291 g; 1.00 mmol) and (S)-1-phenylethylamine (0.121 g; 1.00 mmol) were taken up in 2 ml of isopropanol. The mixture was seeded after stirring at room temperature for 5 minutes. After stirring overnight at ~100° C. a precipitate had formed. This was collected by filtration to give 0.124 g of a white solid, which was enriched in the (S)-enantiomer of the acid (85.91 ee).

The mother liquors after solvent removal gave 0.285 g of a beige-coloured foam, which was enriched in the (R)-enantiomer of the acid (44.61 ea).

EXAMPLE 5

The acid (2.91 g; 1.0 mmol) and (–)-quinine (3.24 g; 1.0 mmol) were taken up in 20 ml of acetone by heating to 40° C. Stirring at 40° C. was continued for 5 minutes, and the solution was then cooled to 15° C. and maintained at this temperature for 16 hours. A seed crystal was added after 5 minutes' stirring at 15° C. The crystals that formed were collected by filtration to give 1.90 g of a white solid, which was enriched in the (S)-enantiomer of the acid (75.2% ee). Two recrystallisations in acetone resulted in a diastereomeric purity of 92%.

The mother liquors from the filtration were evaporated under reduced pressure to give 4.25 g of a beige-coloured solid, which was enriched with the (R)-enantiomer of the acid (43% ee),

We claim:

1. A process for preparing a substantially single isomer of 4-cyano-4-(3,4-dimethoxyphenyl)-5-methylhexanoic acid, or an analogue thereof, which proceeds by means of a classical salt resolution employing an enantiomer, R or S, of a resolving agent selected from the group consisting of 1-phenylethylamine, 1-(1-naphthyl)ethylamine, and (–)-quinine.

2. A process for the synthesis of substantially single enantiomer, R or S, verapamil, or an analogue thereof, comprising preparing a substantially single isomer of 4-cyano-4-(3,4-dimethoxyphenyl)-5-methylhexanoic acid, or an analogue thereof, by means of a classical salt resolution employing an enantiomer, R or S, of a resolving agent selected from the group consisting of 1-phenylethylamine, 1-(1-naphthyl)ethylamine, and (–)-quinine; and subsequent conversion of the product obtained to verapamil, or an analogue thereof.

3. An enantiomeric salt, R or S, of 4-cyano-4-(3,4-dimethoxyphenyl)-5-methylhexanoic acid, or an analogue thereof, wherein the counterion is resolved by employing an enantiomer, R or S, of a resolving agent selected from the group consisting of 1-phenylethylamine, 1-(1-naphthyl)ethylamine, and (–)-quinine.

* * * * *